(12) United States Patent
Najafi

(10) Patent No.: US 10,478,067 B2
(45) Date of Patent: Nov. 19, 2019

(54) IMPLANTABLE SENSING DEVICES AND ANCHORING METHODS THEREFOR

(71) Applicant: Integrated Sensing Systems, Inc., Ypsilanti, MI (US)

(72) Inventor: Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 45 days.

(21) Appl. No.: 15/591,087

(22) Filed: May 9, 2017

(65) Prior Publication Data

US 2017/0319067 A1 Nov. 9, 2017

Related U.S. Application Data

(60) Provisional application No. 62/391,742, filed on May 9, 2016, provisional application No. 62/391,743, filed on May 9, 2016.

(51) Int. Cl.
*A61B 5/02* (2006.01)
*A61B 5/00* (2006.01)
*A61B 5/021* (2006.01)

(52) U.S. Cl.
CPC ........ *A61B 5/0031* (2013.01); *A61B 5/02141* (2013.01); *A61B 5/6882* (2013.01); *A61B 5/02* (2013.01)

(58) Field of Classification Search
None
See application file for complete search history.

(56) References Cited

U.S. PATENT DOCUMENTS

| | | |
|---|---|---|
| 6,968,743 B2 | 11/2005 | Rich et al. |
| 7,317,951 B2 | 1/2008 | Schneider et al. |
| 7,615,010 B1 | 11/2009 | Najafi et al. |
| 7,634,319 B2 | 12/2009 | Schneider et al. |
| 7,686,762 B1 | 3/2010 | Najafi et al. |
| 7,860,579 B2 | 12/2010 | Goetzinger et al. |
| 8,014,865 B2 | 9/2011 | Najafi et al. |
| 8,267,863 B2 | 9/2012 | Najafi et al. |
| 8,322,346 B2 | 12/2012 | Najafi et al. |
| 8,512,252 B2 | 8/2013 | Ludomirsky et al. |
| 8,696,693 B2 | 4/2014 | Najafi et al. |
| 8,715,300 B2 | 5/2014 | Najafi et al. |
| 8,744,544 B2 | 6/2014 | Najafi et al. |

(Continued)

*Primary Examiner* — Ankit D Tejani
(74) *Attorney, Agent, or Firm* — Hartman Global IP Law; Gary M. Hartman; Domenica N.S. Hartman

(57) ABSTRACT

Procedures, implantable wireless sensing devices, and sensor assemblies suitable for monitoring physiological parameters within living bodies. Such sensor assembly includes a sensing device and an anchor for securing the sensing device within a living body. The sensing device comprises a housing having at least one internal cavity and a transducer and electrical circuitry within the at least one internal cavity. The sensing device further comprises an antenna that is within the at least one internal cavity or outside the housing. The housing has at least one additional housing portion in which the transducer, the electrical circuitry, and the antenna are not located. The anchor has a metal portion that surrounds the at least one additional housing portion so as not to surround the transducer, the electrical circuitry, or the antenna.

25 Claims, 10 Drawing Sheets

(56) References Cited

U.S. PATENT DOCUMENTS

| | | | | |
|---|---|---|---|---|
| 2007/0179583 A1* | 8/2007 | Goetzinger | ........ | A61B 17/3468 607/126 |
| 2009/0005656 A1* | 1/2009 | Najafi | .................. | A61B 5/6882 600/301 |
| 2012/0022507 A1* | 1/2012 | Najafi | .................. | A61B 5/0215 606/1 |

* cited by examiner

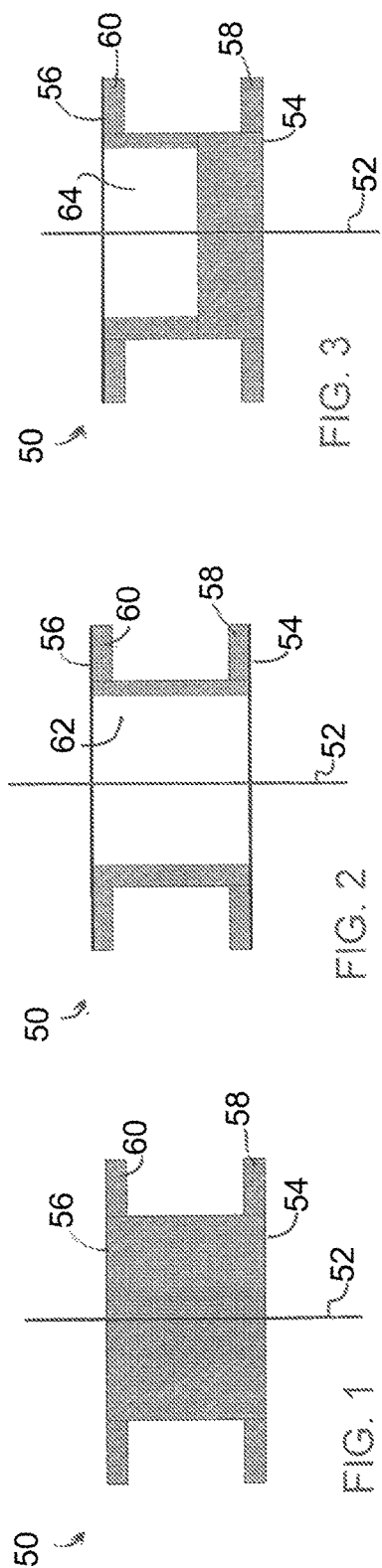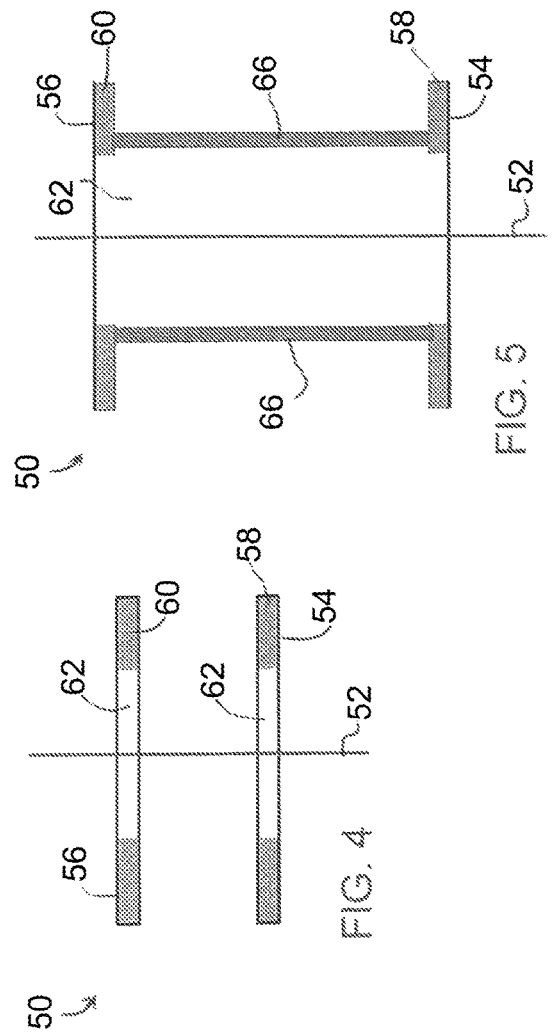

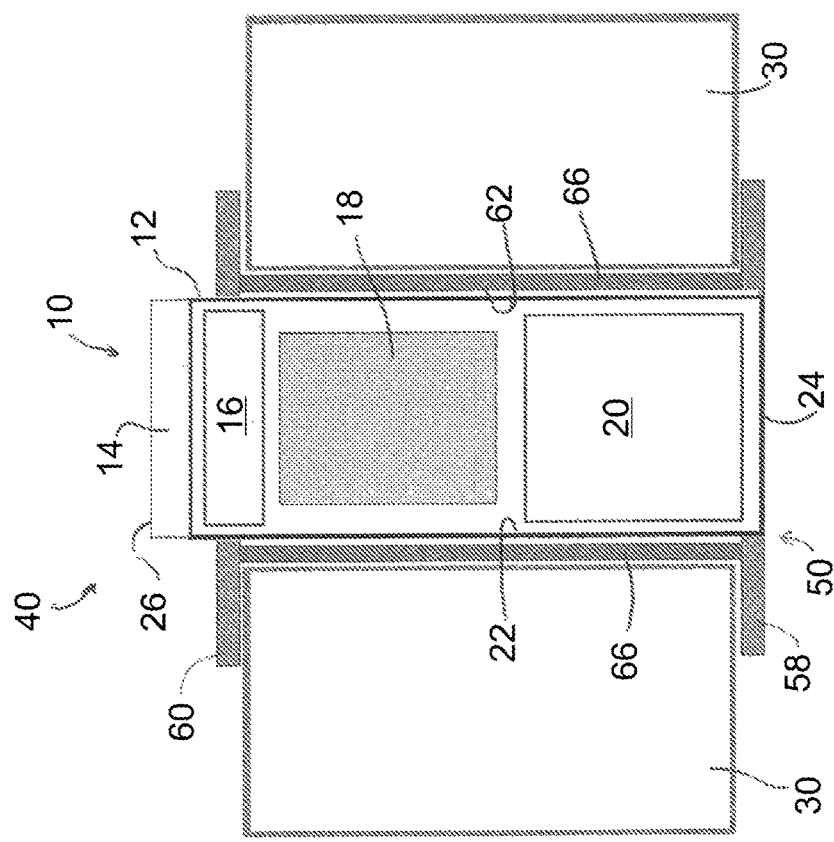

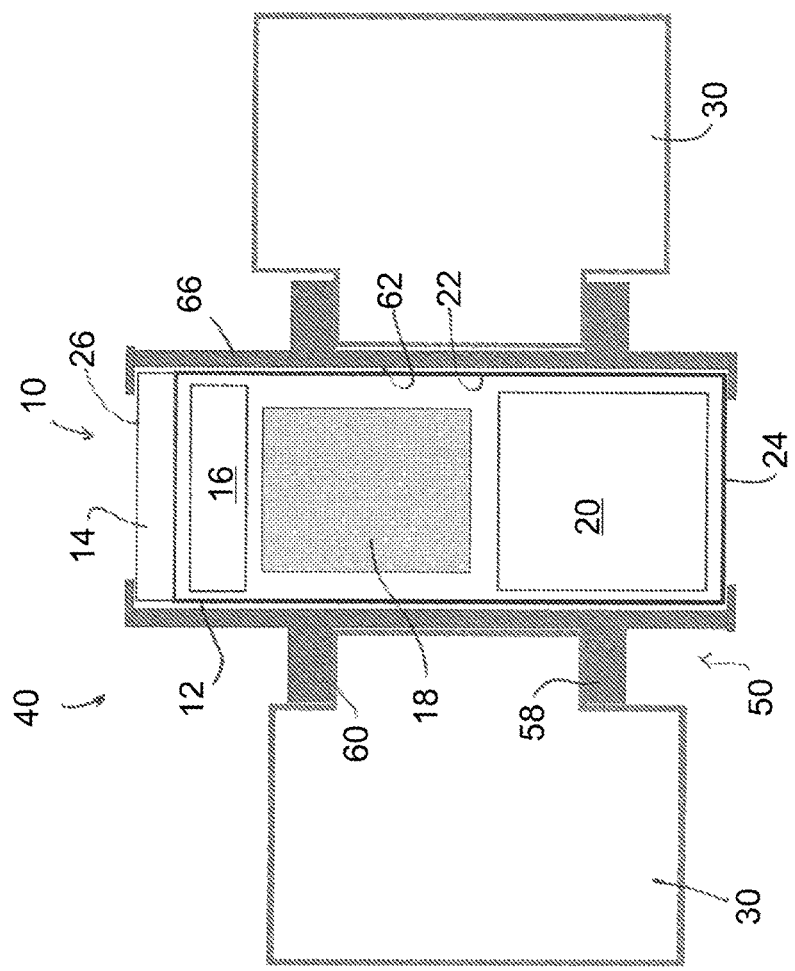

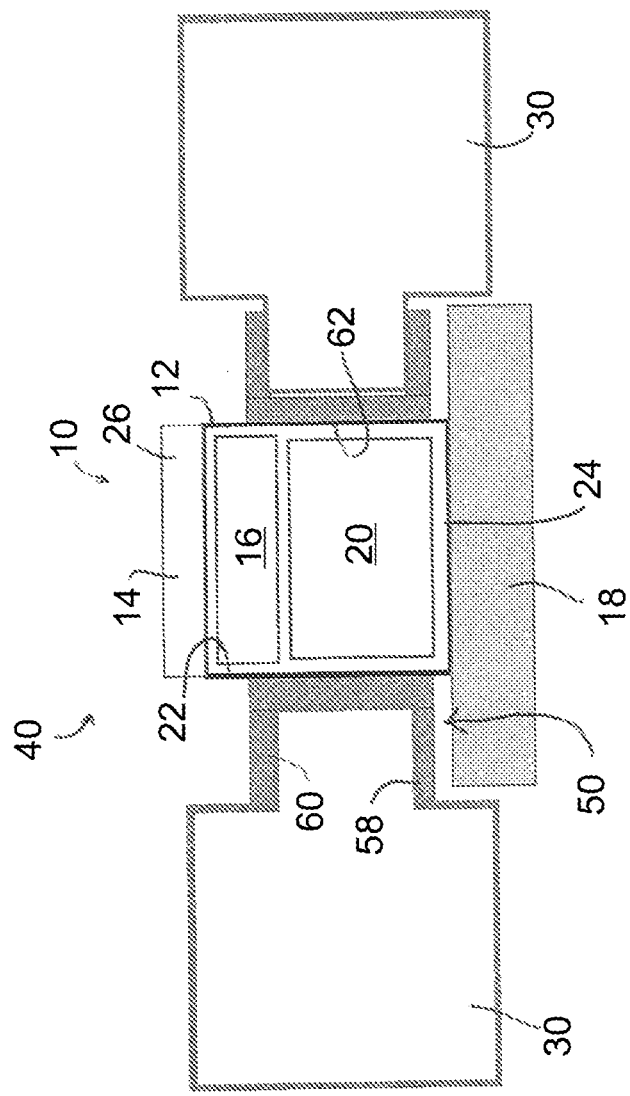

IMPLANTABLE SENSING DEVICES AND ANCHORING METHODS THEREFOR

CROSS REFERENCE TO RELATED APPLICATIONS

This application claims the benefit of U.S. Provisional Application No. 62/391,742, filed May 9, 2016, the contents of which are incorporated herein by reference.

Various patents pertain to procedures, systems, and implantable sensing devices suitable for monitoring physiological parameters within living bodies, as nonlimiting examples, U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. Some of the inventions disclosed in these patents particularly pertain to anchoring and delivery of implantable wireless hermetically-sealed sensing devices by percutaneous methods or minimally invasive surgery (MIS). While the innovations disclosed in these patents can be applied to many different body organs and systems, of particular interest has been placement in the cardiovascular system and especially within or in the vicinity of a heart chamber to monitor one or more physiological parameters within the chamber.

Some of the inventions disclosed in the above-noted patents note the ability of using metallic devices, for example vascular closure devices, atrial septum defect occluder devices (ASD and PFO occluders), and closure paravalvular leak devices, to anchor implantable wireless sensing devices. Nonlimiting examples of such devices include the CELT ACD® produced by Vasorum Ltd. (http://vasorum.ie/) or various devices produced by Occlutech International AB (http://www.occlutech.com/index.php/en/products). However, various problems can be encountered when attempting to anchor an implantable wireless sensing device using such devices, for example, metallic vascular closure devices can have a Faraday-cage effect on a wireless sensing device that can adversely affect the range and quality of tele-powering or wireless communications of the sensing device, and stresses induced in the sensing device caused by its attachment to the closure device can adversely affect the performance of the sensing device, for example, by inducing drift.

BACKGROUND OF THE INVENTION

The present invention generally relates to procedures, implantable wireless sensing devices, and sensor assemblies suitable for monitoring physiological parameters within living bodies.

According to one aspect of the invention, a sensor assembly includes a sensing device and an anchor for securing the sensing device within a living body. The sensing device comprises a housing having at least one internal cavity and a transducer and electrical circuitry within the at least one internal cavity. The sensing device further comprises an antenna that is within the at least one internal cavity or outside the housing. The housing has at least one additional housing portion in which the transducer, the electrical circuitry, and the antenna are not located. The anchor has a metal portion that surrounds the at least one additional housing portion so as not to surround the transducer, the electrical circuitry, or the antenna.

According to another aspect of the invention, a method of measuring a physiological parameter in a blood vessel utilizes a sensor assembly comprising the elements described above.

Other aspects and advantages of this invention will be better appreciated from the following detailed description.

BRIEF DESCRIPTION OF THE DRAWINGS

FIGS. 1 through 5 schematically represent anchors of types that can be used to anchor implantable wireless sensing devices in accordance with nonlimiting embodiments of the invention.

FIGS. 12 through 20 schematically represent various sensor assemblies comprising the anchors of FIGS. 1 through 5 and the sensing devices of FIGS. 7 through 11 in accordance with nonlimiting aspects of the invention.

DETAILED DESCRIPTION OF THE INVENTION

Figure 6:
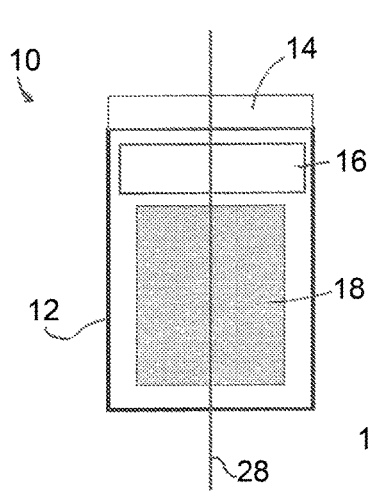
FIG. 6 schematically represents a conventional sensing device.

Illustrated in the drawings are components of monitoring systems that include the implementation of an implantable wireless sensing device configured to be placed within a living body, including internal organs thereof, for monitoring one or more physiological parameters. Physiological parameters of particular interest include but are not limited those relating to the function of the circulatory, respiratory, urinary, and nervous systems, and organs of particular interest include but are not limited to the heart, blood vessels, liver, brain (e.g., intracranial), kidneys, lungs, and bladder. Notable particular examples relating to the heart include any of the four heart chambers (particularly the left ventricle and left atrium), and notable examples relating to blood vessels include the inferior vena cava and blood vessels associated with the heart and lungs.

There are also advantageous aspects relating to the placement of an implantable sensing device, such as an IHM sensor or other type of sensor, in the inferior vena cava. The largest vein in the human body, the inferior vena cava collects blood from veins serving the tissues inferior to the heart and returns this blood to the right atrium of the heart. Although the vena cava is very large in diameter, its walls are thin due to the low pressure exerted by venous blood. The inferior vena cava forms at the superior end of the pelvic cavity when the common iliac veins unite to form a larger vein. From the pelvis, the inferior vena cava ascends through the posterior abdominal body wall just to the right of the vertebral column. Along its way through the abdomen, blood from the internal organs joins the inferior vena cava through a series of large veins, including the gonadal, renal, suprarenal and inferior phrenic veins. Blood from the tissues of the lower back, including the spinal cord and muscles of the back, enters the vena cava through the lumbar veins. Many smaller veins also provide blood to the vena cava from the tissues of the abdominal body wall. Upon reaching the heart, the inferior vena cava connects to the right atrium on its posterior side, inferior to the connection of the superior vena cava. The inferior vena cava and its tributaries drain blood from the feet, legs, thighs, pelvis and abdomen and deliver this blood to the heart. Many one-way venous valves help to move blood through the veins of the lower extremities against the pull of gravity. Blood passing through the veins is under very little pressure and so must be pumped toward the heart by the contraction of skeletal muscles in the legs and by pressure in the abdomen caused by breathing. Venous valves help to trap blood between muscle contractions or breaths and prevent it from being pulled back down towards the feet by gravity.

Preferred aspects of the present invention include the ability to provide implantable wireless sensing devices suitable for monitoring one or more physiological parameters within blood vessels, including those mentioned above. The physical footprint of such an implantable wireless sensing device is preferably limited to the sensing device, an anchor that secures the sensing device to or within the vein, and optionally a separate antenna that wirelessly transmits data and other communications to a remote device, such as a readout unit, which may also tele-power the sensing device. The physical footprint of such an implantable wireless sensing device can be far smaller than monitoring systems that must be physically connected to a relatively large remote transmitting device, for example, as in the case of the LVP-1000 Left Ventricle Pressure Monitoring System offered by Transoma Medical, Inc. Implantable wireless sensing device utilized by the invention may employ resonant, passive, or active communication schemes described in prior patents, including but not limited to those disclosed in U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. The drawings schematically represent various implantable wireless sensing devices as comprising a single hermetically-sealed housing that contains a transducer and electronic circuitry, for example, an application specific integrated circuit (ASIC), which operate in combination with an antenna to transmit and receive data.

In the drawings, the antenna is represented as comprising a coil (e.g., copper windings) wrapped around a core (e.g., ferrite), though other antenna configurations and materials are foreseeable. The transducer, which is located at a proximal end of the housing, is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. A particular but nonlimiting example of a suitable transducer for hemodynamic monitoring of various blood pressures within the cardiovascular system is a MEMS capacitive pressure sensor for sensing pressure, though other materials and any variety of sensing elements, e.g., capacitive, inductive, resistive, piezoelectric, etc., could be used. For example, the transducer could be configured to sense temperature, flow, acceleration, vibration, pH, conductivity, dielectric constant, and chemical composition, including the composition and/or contents of a biological fluid, for example, oxygen, carbon dioxide, glucose, gene, hormone, or gas content of the fluid.

The sensing device may be powered with a battery or other power storage device, but in preferred embodiments is powered entirely by a remote device that is not configured for implantation, such as a readout unit. Such a readout unit may be configured to receive an output signal from the sensing device, process the signal, and relay the processed signal as data in a useful form to a user. Because the sensing device is equipped with a built-in antenna, the device requires only an anchor for implantation and does not require a wire, cable, tether, or other physical component that conducts the output of the sensing device to a separate location where another component utilizes the output of the sensing device and/or transmits the output of the sensing device to a location outside the body of the patient.

In the drawings, consistent reference numbers are used to identify functionally equivalent structures of various implantable wireless sensing devices 10 and to identify functionally equivalent structures of various anchors 50 that are adapted to secure the sensing devices 10. As noted above, the drawings schematically represent the sensing devices 10 as comprising a single hermetically-sealed housing 12 that contains a transducer 14 and electronic circuitry 16, for example, an application specific integrated circuit (ASIC), which operate in combination with an antenna 18 to transmit and receive data. The sensing devices 10 differ from each other by the placement of the antenna 18 within or outside the housing 12. The anchors 50 may be chosen in part on the basis of the placement of the antenna 18 relative to the housing 12. The housings 12 of the sensing devices 10 are configured to comprise a housing portion 20 that is in addition to portions of the housing 12 in which one or more internal cavities 22 are located that contain the transducer 14 and antenna 18. As such, the additional housing portion 20 is not required to contain, and preferably does not contain, any component relating to the operation of the transducer 14 and the transmission of data to and from the sensing device 10 via the antenna 18, and therefore a cavity is not required to be present in the additional housing portion 20. Furthermore, such an additional housing portion 20 may form a distal end 24 of the housing 12, i.e., opposite of the proximal end 26 of the housing 12 where the transducer 14 is located such that the antenna 18 is located between the transducer 14 and the additional housing portion 20, or may be located between the transducer 14 and the antenna 18, or may be a combination of both (i.e., the additional housing portion 20 may comprise two spaced-apart portions 20) that are connected together only through the housing 12 or by the anchor 50. The additional housing portion 20 may be integrally formed as an indiscrete region of the housing 12, or separately formed and directly attached to the housing 12, or separately formed and indirectly attached to the housing 12 with the anchor 50.

Instead of containing components relating to the operations of the transducer 14 and antenna 18 or to data transmission, the additional housing portion 20 can be dedicated to the attachment of an anchor 50 to the sensing device 10. In particular, the additional housing portion 20 is particularly well suited for enabling the sensing device 10 to be secured with metallic anchors 50, including but not limited to vascular closure devices, atrial septum defect occluder devices (ASD and PFO occluders), and closure paravalvular leak devices, such that the transducer 14 and antenna 18 are sufficiently remote from the anchor 50 that metallic portions of the anchor 50 do not interfere with their operations. As an example, the additional housing portion 20 preferably creates a spacial axial distance between the antenna 18 and a metallic anchor 50 (or metallic portions thereof) to reduce Faraday-cage effects otherwise caused by metal, and creates a spacial axial distance between a metallic anchor 50 and the transducer 14 to reduce if not avoid stresses that could mechanically interfere with the operation of the transducer 14, for example, cause a drift in its signal output.

The attachment of the sensing device 10 to the anchor 50 can be accomplished in different ways, including but not limited to one or more of the following: attachment by a third material (e.g., glue, epoxy, etc.), mechanical grips, threads (e.g., the housing 12 is threaded into the anchor 50), using a discrete attachment member (e.g., made from PEEK or NiTi material), compression, thermal compression, or a mechanical attachment feature of the sensing device 10 or anchor 50 (e.g., fingers, loops, spirals, etc.).

FIGS. 1 through 5 schematically represent anchors 50 that have a generally cylindrical outline and define an axis 52 that may be an axis of rotational symmetry. Each of the anchors 50 has distal and proximal ends 54 and 56, at which axial spaced flanges or rings 58 and 60 are present. The anchors 50 are solid between their distal and proximal ends 54 and 56, i.e., lack an internal hole or cavity (FIG. 1), or have a through-hole 62 (FIG. 2), or have a blind hole 64 (FIG. 3), or comprise two discrete rings 58 and 60 that are not connected to each other but define two separate through-holes 62 (FIG. 4), or comprise two discrete rings 58 and 60 that are interconnected to each other by longitudinal legs 66 to define a through-hole 62 within the anchor 50 (FIG. 5). In the embodiments of FIGS. 2 through 5, the anchors 50 are sized to accommodate a sensing device 10 within their respective through-hole 62, blind hole 64, rings 58 and 60, and/or legs 66. In the embodiment of FIG. 1, a sensing device 10 may be attached to either axial end 54 or 56 of the anchor 50. Other anchor 50 configurations are also within the scope of the invention. The anchors 50 may be formed or fabricated from a variety of materials, including but not limited to metals including stainless steels and shape-memory alloys (e.g., NiTi alloys), and/or polymers including PEEK.

FIGS. 6 through 11 schematically represent sensing devices 10 that each defines an axis 28 that may be an axis of rotational symmetry. The housings 12 of the sensing devices 10 are sized and shaped for attachment to one or more of the anchors 50 shown in FIGS. 1 through 5, for example, by attachment to either axial end 54 or 56 of the anchor 50 of FIG. 1, or placement in the through-hole 62, blind hole 64, rings 58 and 60, or legs 66 of the anchors 50 of FIGS. 2 through 5. The sensing device 10 of FIG. 6 will be referred to herein as a conventional sensing device 10, in that its housing 12 is represented as being sized to accommodate the transducer 14, antenna 18, and electronic circuitry 16 within an internal cavity 22 defined by the housing 12, with little additional cavity space not occupied by the transducer 14, antenna 18, and electronic circuitry 16. The sensing devices 10 of FIGS. 7 through 11 differ from the conventional sensing device 10 of FIG. 6 as well as from each other by the placement of the antenna 18 within (FIGS. 6 through 9 and 11) or outside (FIG. 10) their respective housings 12, and the inclusion of at least one additional housing portion 20 that is in addition to the internal cavity (or cavities) 22 that contain(s) the transducer 14, antenna 18, and electronic circuitry 16. The placement of the antenna 18 outside of the housing 12 in FIG. 10 allows for the diameter of the antenna 18 to be larger from the diameter of the housing 12. Because the diameter of the antenna 18 greatly affects the tele-powering and tele-communication range of the sensing device 10, the wider diameter antenna 18 of FIG. 10 may eliminate the requirement for a ferrite coil, so that the sensing device 10 requires only a coil.

Figure 7:
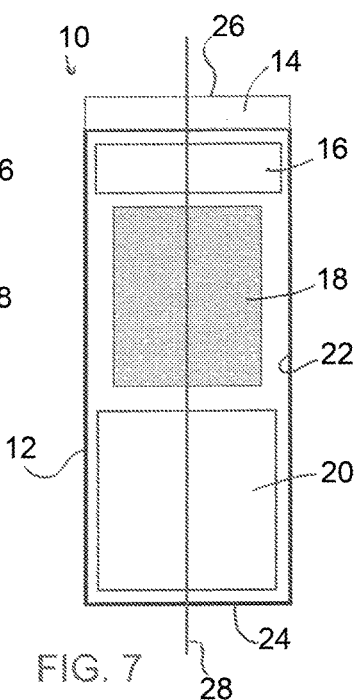
FIGS. 7 through 11 schematically represent sensing devices in accordance with nonlimiting aspects of the invention.
Figure 8:
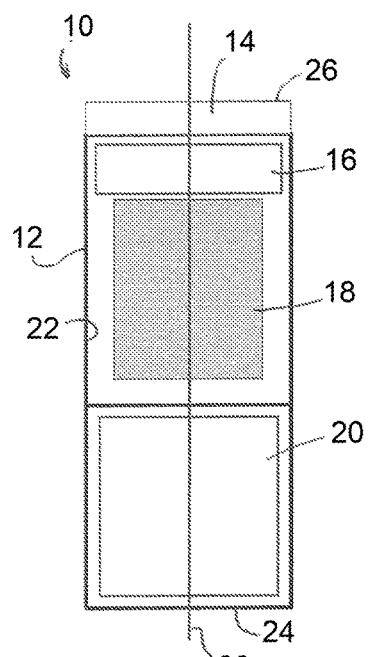
Figure 9:
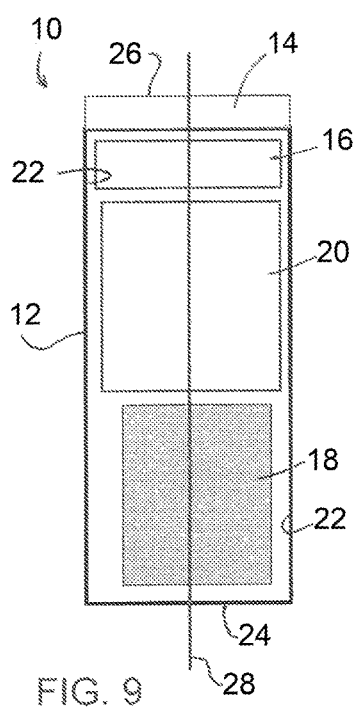
Figure 10:
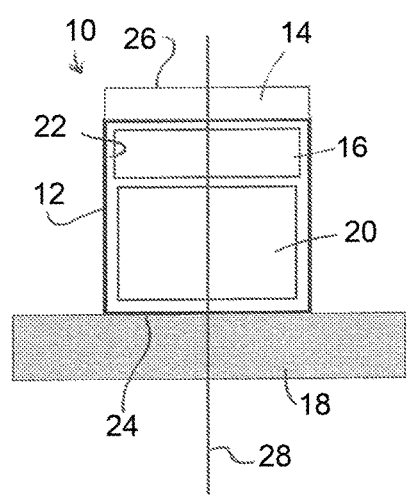
Figure 11:
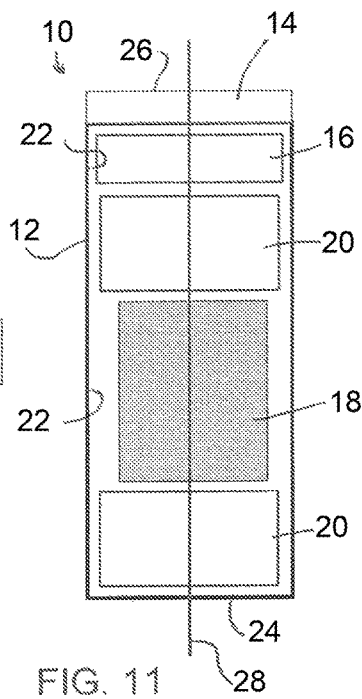

The additional housing portions 20 are not required to contain any component relating to the operation of the sensing device 10 or its transducer 14, antenna 18, or electronic circuitry 16, and therefore a cavity is not required to be present in the additional housing portions 20. As such, the representations of the additional housing portions 20 in the drawings do not necessarily (though may) indicate a cavity, but instead more generally indicate regions of their housings 12 that may entirely be a cavity-free solid. The additional housing portion 20 is represented in FIGS. 7 and 8 as located in or forming the distal end 24 of the housing 12 opposite its proximal end 26 where the transducer 14 and electronic circuitry 16 are located, such that the antenna 18 is located between the additional housing portion 20 and the transducer 14 and electronic circuitry 16. The additional housing portion 20 is represented in FIGS. 9 and 10 as located within a midsection of the housing 12 between the antenna 18 at the distal end 24 of the housing 12 and the transducer 14 and electronic circuitry 16 at the proximal end 26 of the housing 12. The additional housing portion 20 is represented in FIG. 11 as comprising two spaced-apart portions 20, a first between the antenna 18 located within the midsection of the housing 12 and the transducer 14 and electronic circuitry 16 at the proximal end 26 of the housing 12, and a second between the antenna 18 and the distal end 24 of the housing 12. The additional housing portions 20 of FIGS. 7 and 9 through 11 are integrally formed as an indiscrete region of the housing 12, whereas the additional housing portion 20 of FIG. 8 is separately formed and directly attached to the distal end 24 of the housing 12.

Figure 13:
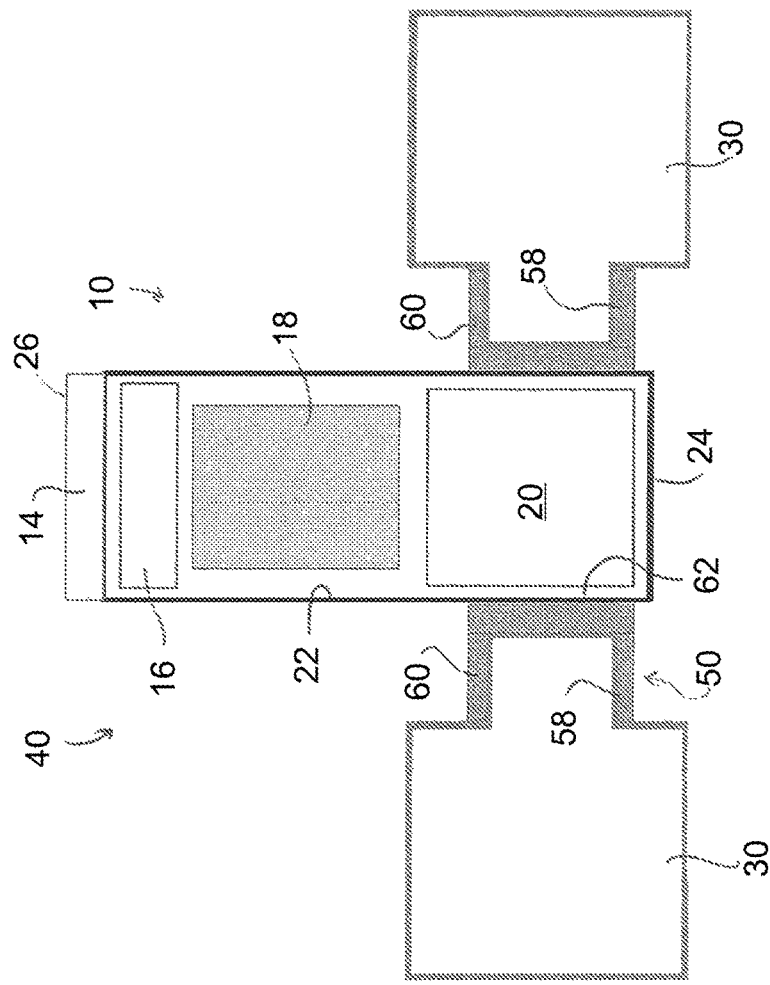
Figure 12:
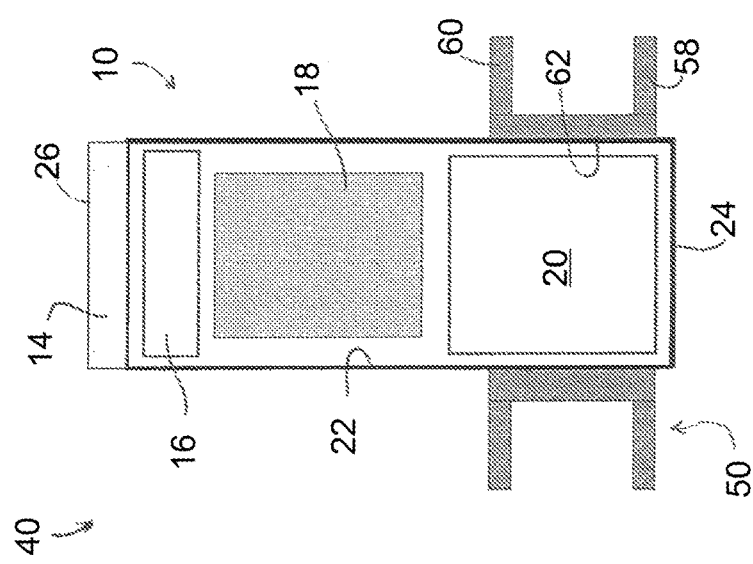

FIG. 12 represents a sensor assembly 40 comprising the sensing device 10 of FIG. 7 assembled with the anchor 50 of FIG. 2, and FIG. 13 represents the sensor assembly 40 of FIG. 12 implanted in a wall 30 of an organ such that the anchor 50 secures the sensing device 10 to the organ wall 30. As evident from FIG. 13, the distal end 24 of the sensing device 10 sufficiently extends through the through-hole 62 of the anchor 50 so that the anchor 50 contacts and surrounds or circumscribes only that part of the housing 12 that is formed by the additional housing portion 20 or otherwise in which the additional housing portion 20 is present, such that the anchor 50 does not have a negative effect or has a minimal negative effect on the functions of the internal antenna 18 and transducer 14. In FIGS. 12 and 13, the anchor 50 is radially aligned with the additional housing portion 20 with respect to the axis 28 of the housing 12 (FIG. 7).

Figure 14:
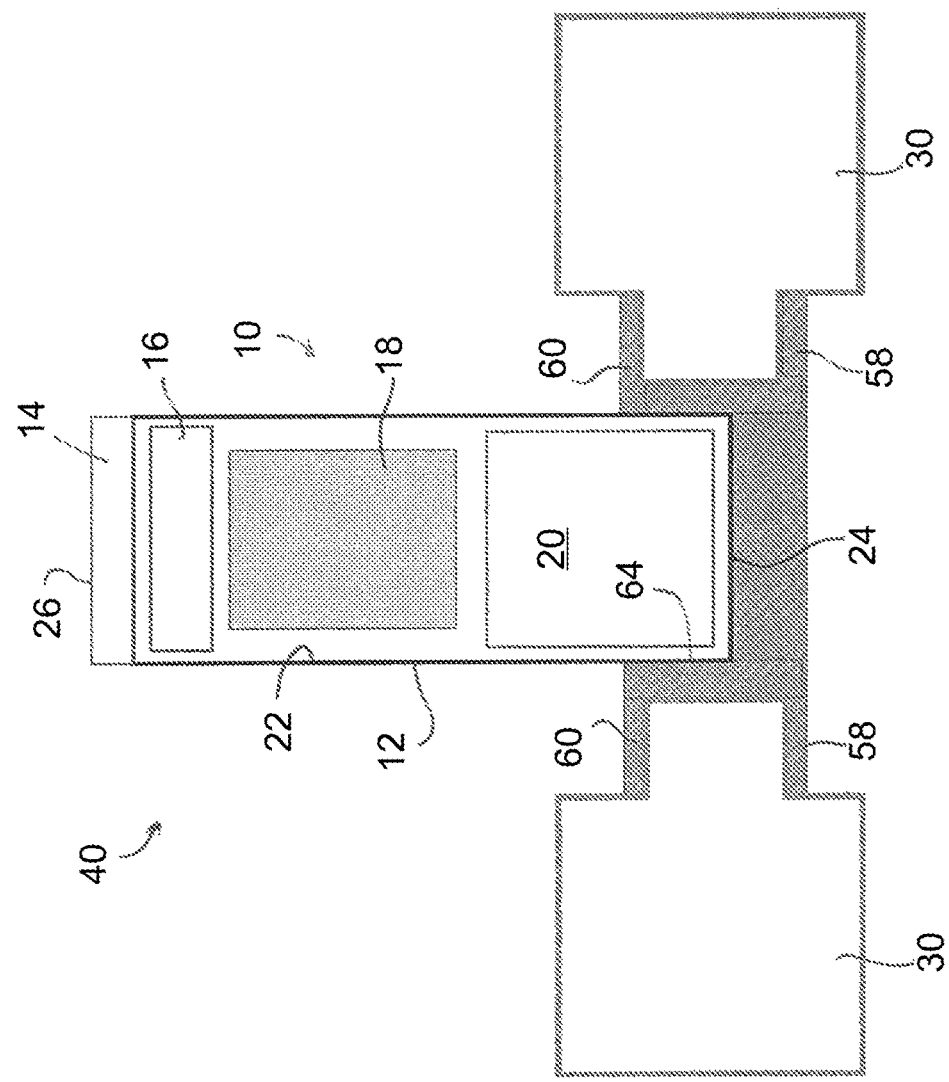
Figure 15:
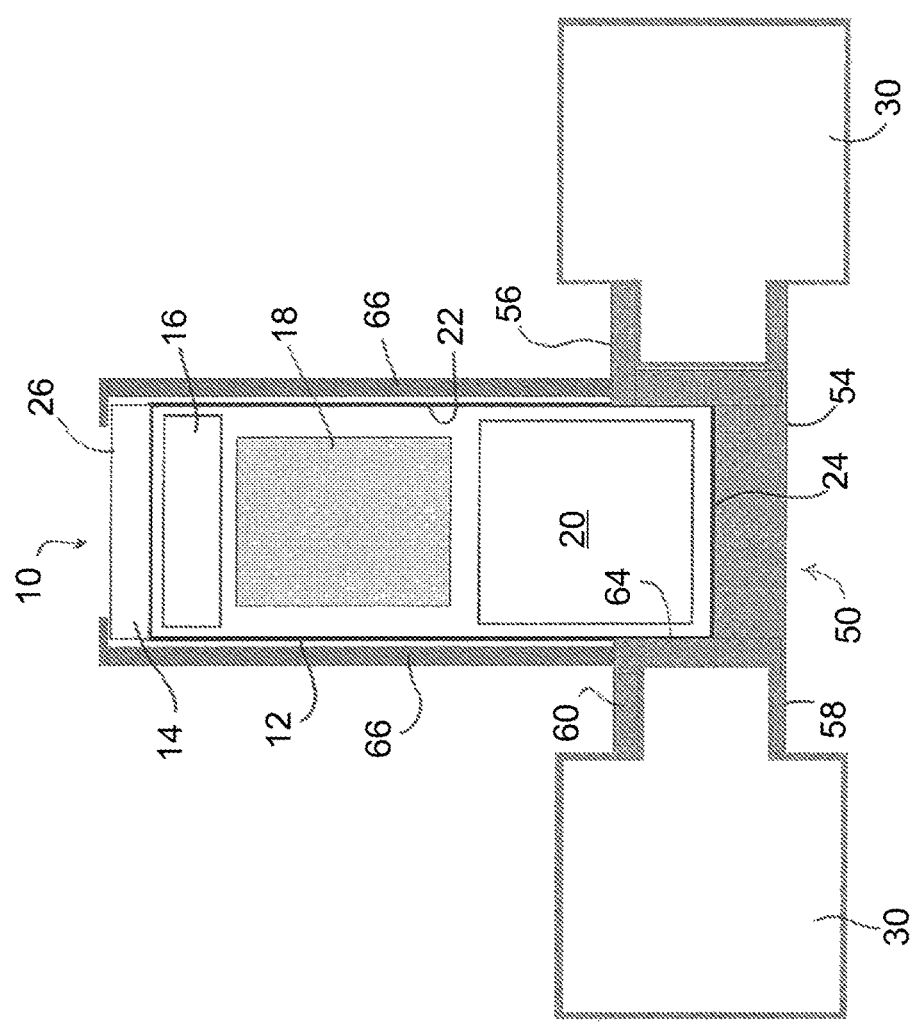

FIG. 14 represents a sensor assembly 40 comprising the sensing device 10 of FIG. 7 assembled with the anchor 50 of FIG. 3, and shows the sensor assembly 40 implanted in a wall 30 of an organ with the anchor 50. As evident from FIG. 14, the distal end 24 of the sensing device 10 is received in the blind hole 64 of the anchor 50 so that the anchor 50 contacts and surrounds or circumscribes only the distal end 24 of the housing 12, which is formed by or contains the additional housing portion 20. FIG. 15 represents a sensor assembly 40 similar to that of FIG. 14 but whose anchor 50 has been modified to have fingers or legs 66 that extend from the axial end 56 of the anchor 50 in which the blind hole 64 is formed and capture the proximal end 26 of the housing 12 to better secure the sensing device 10.

Figure 16:
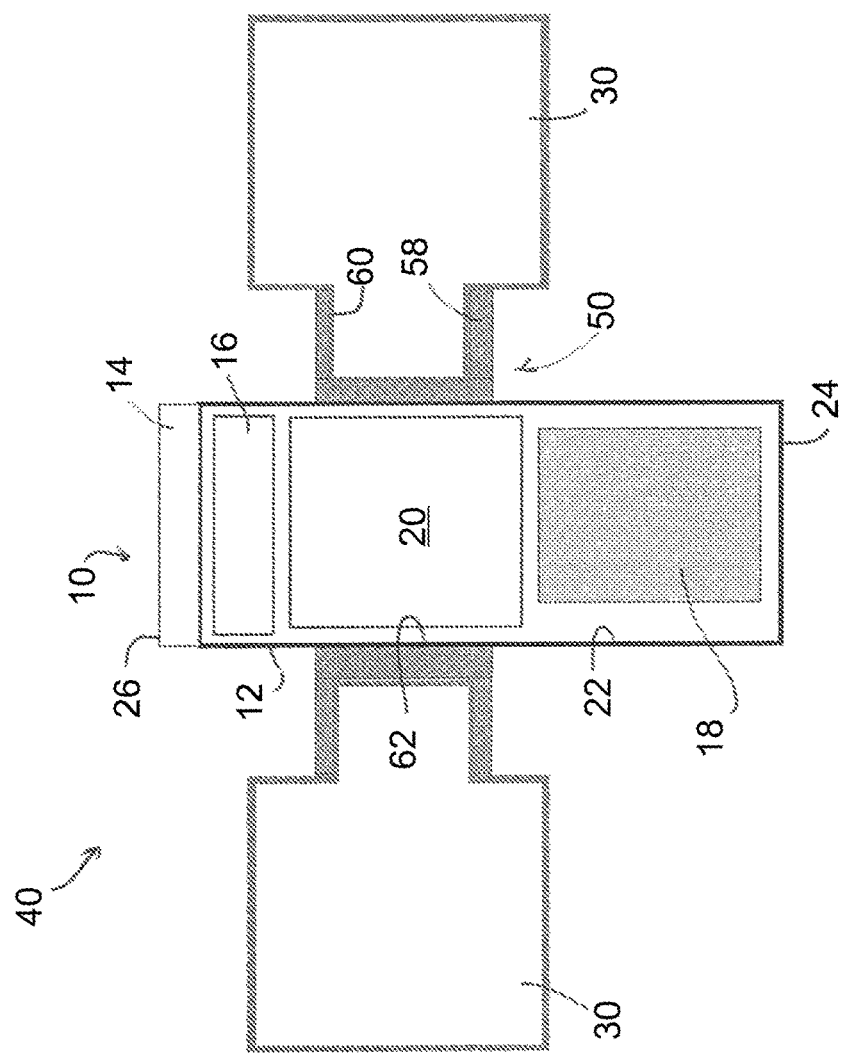

FIG. 16 represents a sensor assembly 40 comprising the sensing device 10 of FIG. 9 assembled with the anchor 50 of FIG. 2, and shows the sensor assembly 40 implanted in a wall 30 of an organ with the anchor 50. The distal and proximal ends 24 and 26 of the sensing device 10 are located outside of the through-hole 62 of the anchor 50, which contacts and surrounds or circumscribes only the midsection of the housing 12 that is formed by the additional housing portion 20 or otherwise in which the additional housing portion 20 is present. In FIG. 16, the anchor 50 is radially aligned with the additional housing portion 20 with respect to the axis 28 of the housing 12 (FIG. 9).

Figure 17:
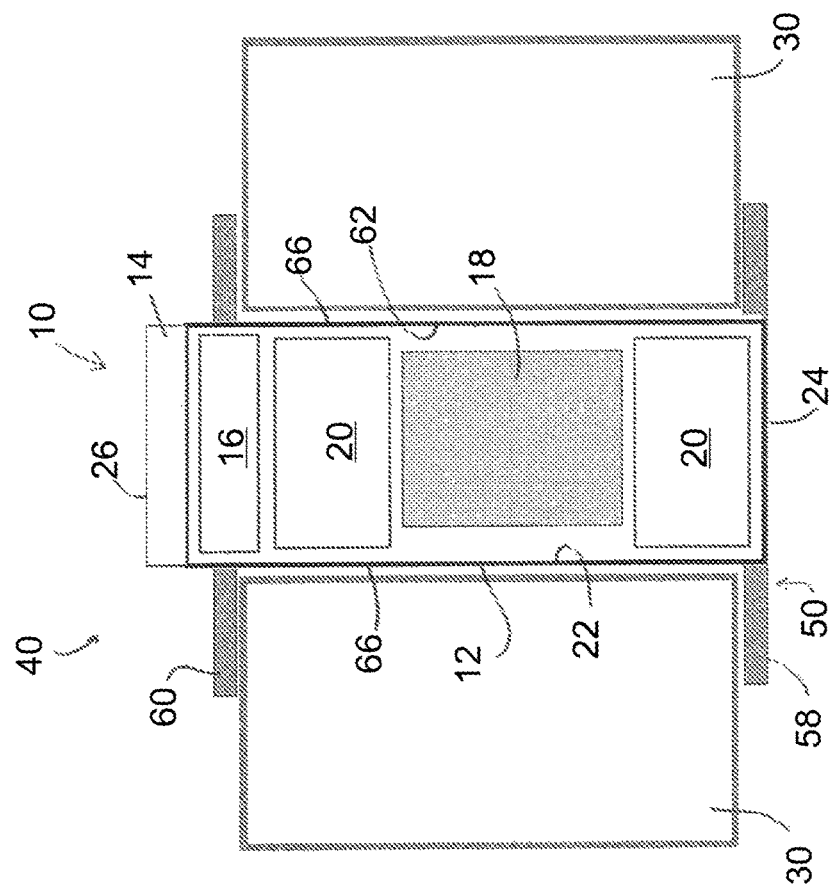

FIG. 17 represents a sensor assembly 40 comprising the sensing device 10 of FIG. 11 assembled with the anchor 50 of FIG. 5, and shows the sensor assembly 40 implanted in a wall 30 of an organ with the anchor 50. The distal and proximal ends 24 and 26 of the sensing device 10 are located at or adjacent opposite ends of the through-hole 62 of the anchor 50, which surrounds or circumscribes the housing 12 between its distal and proximal ends 24 and 26. As a result, the internal antenna 18 (located at the midsection of the housing 12) is not surrounded by either ring 58 and 60 of the anchor 50, but instead is only surrounded or circumscribed by the longitudinal legs 66 that interconnect the rings 58 and 60. In this embodiment, the rings 58 and 60 may be metallic, but the legs 66 are preferably formed of a nonmetallic material so as to not have a Faraday-cage effect on the antenna 18. FIG. 18 represents a sensor assembly 40 comprising the anchor 50 of FIG. 5 similar to FIG. 17, but assembled with the sensing device 10 of FIG. 7. The distal and proximal ends 24 and 26 of the sensing device 10 are again located at opposite ends of the through-hole 62 of the anchor 50, and the internal antenna 18 (located near the proximal end 26 of the housing 12) is only surrounded or circumscribed by the longitudinal legs 66 and is not surrounded by either ring 58 or 60.

FIG. 19 represents a sensor assembly 40 in which the sensing device 10 of FIG. 7 assembled with a modified version of the anchor 50 of FIG. 5, in which the longitudinal legs 66 axially extend and protrude beyond both rings 58 and 60 of the anchor 50. The internal antenna 18 (located at the midsection of the housing 12) is predominantly (though not exclusively) surrounded or circumscribed by the longitudinal legs 66 that interconnect rings of the anchor 50. Similar to FIG. 17, though the rings 58 and 60 may be metallic, the legs 66 are preferably formed of a nonmetallic material so as to not have a Faraday-cage effect on the antenna 18.

FIG. 20 represents a sensor assembly 40 comprising the sensing device 10 of FIG. 10 assembled with the anchor 50 of FIG. 2, and shows the sensor assembly 40 implanted in a wall 30 of an organ with the anchor 50. The distal and proximal ends 24 and 26 of the sensing device 10 are located outside of the through-hole 62 of the anchor 50, which contacts and surrounds or circumscribes the region of the housing 12 formed by the additional housing portion 20 or otherwise in which the additional housing portion 20 is present and predominant. As a result, the external antenna 18 of the sensing device 10 is not surrounded or circumscribed by any portion of the anchor 50.

A notable advantage of sensor assemblies 40 of the types described above include the capability of effective long-term monitoring of the cardiovascular system and organs. Data obtained with the sensing devices 10 can be used for multiple purposes, including but limited to management of cardiac diseases, such as congestive heart failure, arrhythmia, structural heart diseases, congenital heart diseases, patients with single functioning ventricle, hypotension, hypertension, etc., and long-term management of patients. Data from the sensing devices 10 may be sampled at home, at a doctor's office, in a surgery room, during post-op stay including ICU, and during hospital stay.

Sensor assemblies 40 of the types represented in FIGS. 12 through 20 can be implanted in various ways. For example, if implanted in an organ, one of the assemblies may be implanted in the wall 30 of the organ so that the proximal end 26 of the sensor housing 12 slightly protrudes into the organ, with the result that the sensor assembly 40 has little or no effect on blood flow through the organ. Alternatively, it is foreseeable that the entire sensor assembly 40 may be placed inside an organ, in which case an anchor 50 may be used to secure the sensing device 10 so that it is centrally located within the organ but is spaced apart from the walls 30 of the organ by legs or arms of the anchor 50 so as to have little if any effect on blood flow. For example, the anchor 50 can be equipped with one or more loops, fingers, spirals, screws, etc., that secure the sensing device 10 to oppositely-disposed walls 30 of the organ. Alternatively, the anchor 50 may be stitched to the wall 30 of the organ, such as with an anchor 50 disclosed in U.S. Pat. No. 9,168,005

The delivery of sensing assemblies 40 of the types described above can be accomplished by percutaneous delivery, catheter delivery (preferably through the femoral vein), minimally invasive approaches, surgical approaches, or combinations thereof. The delivery procedure may be a standalone procedure or performed as part of another procedure.

While the invention has been described in terms of particular embodiments, it should be apparent that alternatives could be adopted by one skilled in the art. For example, the sensing devices 10, anchors 50, and sensor assemblies could differ in appearance and construction from the embodiments described herein and shown in the drawings, functions of certain components of the the sensing devices 10, anchors 50, and sensor assemblies could be performed by components of different construction but capable of a similar (though not necessarily equivalent) function, and appropriate materials could be substituted for those noted. In addition, the invention encompasses additional or alternative embodiments in which one or more features or aspects of different disclosed embodiments may be combined. Accordingly, it should be understood that the invention is not necessarily limited to any embodiment described herein or illustrated in the drawings. It should also be understood that the phraseology and terminology employed above are for the purpose of describing the illustrated embodiments, and do not necessarily serve as limitations to the scope of the invention. Therefore, the scope of the invention is to be limited only by the following claims.

The invention claimed is:

1. A sensor assembly comprising:
   a sensing device comprising a housing having at least one internal cavity and a transducer and electrical circuitry within the at least one internal cavity, the sensing device further comprising an antenna that is within the at least one internal cavity or outside the housing, the housing having at least one additional housing portion in which the transducer, the electrical circuitry, and the antenna are not located; and
   an anchor for securing the sensing device within a living body, the anchor having an axis, a proximal end, a distal end axially spaced apart from the proximal end, and first and second rings that are axially spaced apart, surround the axis, and define flanges that extend radially from the axis, the anchor having metallic portions and optionally nonmetallic portions, at least one of the first and second rings being a first metallic portion of the metallic portions of the anchor and circumscribing the at least one additional housing portion so as not to surround the transducer, the electrical circuitry, or the antenna, wherein the antenna is not circumscribed by any of the metallic portions of the anchor.

2. A method of measuring a physiological parameter in an organ, the method comprising implanting the sensor assembly of claim 1 within the organ or in a wall thereof.

3. The method of claim 2, wherein the organ is a blood vessel.

4. The method of claim 3, wherein the blood vessel is a vein.

5. The method of claim 3, wherein the blood vessel is the inferior vena cava.

6. The method of claim 3, wherein the blood vessel is a blood vessel associated with the heart or lungs.

7. The method of claim 2, wherein the organ is the heart.

8. The method of claim 7, wherein the sensor assembly is implanted in a septum of a heart chamber.

9. The method of claim 2, wherein the sensor assembly is implanted so as to serve as an occluder in the wall of the organ.

10. The method of claim 9, wherein the occluder is a vascular closure device, or an atrial septum defect occluder device, or a paravalvular leak closure device.

11. The method of claim 2, wherein the method comprises delivering the sensing assembly to the organ by percutaneous delivery, catheter delivery, a minimally invasive procedure, a surgical procedure, or a combination thereof.

12. The sensor assembly of claim 1, wherein the transducer is at a first end of the sensing device, the additional housing portion is at an oppositely-disposed second end of the sensing device, and the electrical circuitry and the antenna are between the transducer and the additional housing portion.

13. The sensor assembly of claim 12, wherein the additional housing portion is integrally formed as an indiscrete region of the housing at the second end of the sensing device.

14. The sensor assembly of claim 12, wherein the additional housing portion is separately formed and directly attached to the housing at the second end of the sensing device.

15. The sensor assembly of claim 1, wherein the transducer is at a first end of the sensing device, the antenna is at an oppositely-disposed second end of the sensing device, and the additional housing portion is between the transducer and the antenna.

16. The sensor assembly of claim 15, wherein the antenna is within the internal cavity.

17. The sensor assembly of claim 15, wherein the antenna is outside the housing.

18. The sensor assembly of claim 1, wherein the transducer is at a first end of the sensing device, the additional housing portion comprises a first additional housing portion at an oppositely-disposed second end of the sensing device and a second additional housing portion at the first end of the sensing device, and the antenna is between the first and second additional housing portions.

19. The sensor assembly of claim 1, wherein the anchor has a cylindrical outline and the first and second rings define the distal and proximal ends of the anchor.

20. The sensor assembly of claim 1, wherein the first and second rings define the distal and proximal ends of the anchor, the anchor between the first and second rings is a solid cylinder and lacks an internal hole or cavity that axially extends between the first and second rings, and the distal or proximal end of the anchor is defined by a surface with the sensing device attached thereto.

21. The sensor assembly of claim 1, wherein the anchor has a through hole or a blind hole at the proximal end, the additional housing portion is disposed in the through hole or the blind hole axially between the first and second rings, and the transducer, the electrical circuitry, and the antenna are disposed outside of the through hole or the blind hole.

22. The sensor assembly of claim 1, wherein the first and second rings are discrete rings that define two separate through-holes and define the distal and proximal ends of the anchor.

23. The sensor assembly of claim 22, wherein the first and second rings are not directly connected to each other but are solely interconnected with each other by the housing of the sensing device, the additional housing portion, the electrical circuitry, and the antenna are disposed within the through hole and axially disposed between the first and second rings, the transducer is disposed outside of the through hole, and the antenna is not circumscribed by either of the first and second rings.

24. The sensor assembly of claim 22, wherein the anchor has the nonmetallic portions and comprises longitudinal legs formed of the nonmetallic portions, the first and second rings are not directly connected to each other but are interconnected with each other by the longitudinal legs of the anchor to define a through-hole within the anchor, the additional housing portion, the electrical circuitry, and the antenna are disposed within the through hole, circumscribed by the longitudinal legs, and axially disposed between the first and second rings, the transducer is disposed outside of the through hole, and the antenna is not circumscribed by either of the first and second rings.

25. The sensor assembly of claim 1, wherein the anchor has the nonmetallic portions and comprises longitudinal legs that are formed of the nonmetallic portions and extend axially from the first ring to define a through-hole within the anchor, the transducer, the electrical circuitry, and the antenna are disposed within the through hole and are circumscribed by the longitudinal legs, and the additional housing portion is surrounded by one of the first and second rings.

* * * * *